United States Patent [19]

Lewis

[11] Patent Number: 4,563,189

[45] Date of Patent: Jan. 7, 1986

[54] TREATMENT OF FIBERS WITH ARYLATING AGENTS TO ENHANCE DISPERSE DYEABILITY

[75] Inventor: David M. Lewis, Otley, England

[73] Assignee: Wool Development International Ltd., London, England

[21] Appl. No.: 577,131

[22] Filed: Feb. 6, 1984

[30] Foreign Application Priority Data

Feb. 11, 1983 [GB] United Kingdom ............... 8303850

[51] Int. Cl.$^4$ ........................ D06M 13/34; D06P 5/22
[52] U.S. Cl. .......................................... 8/493; 8/471; 8/120; 8/128 R; 8/917; 8/918; 8/924; 260/455 R; 544/180; 564/209
[58] Field of Search ....................... 8/493, 120, 128 R

[56] References Cited

U.S. PATENT DOCUMENTS

| | | | |
|---|---|---|---|
| 3,278,253 | 10/1966 | Weckler et al. ......................... | 8/493 |
| 4,113,431 | 9/1978 | Terada et al. ........................... | 8/120 |
| 4,142,853 | 3/1979 | Terada et al. ........................... | 8/120 |
| 4,286,958 | 9/1981 | Fujiu et al. .............................. | 8/471 |
| 4,313,732 | 2/1982 | Teague et al. .......................... | 8/541 |
| 4,392,265 | 7/1983 | Fujiu et al. .............................. | 8/120 |

OTHER PUBLICATIONS

Bell, V. A. et al., J. Soc. Dyers and Colourists, 1984, 100, (No. 7/8), 223–231.

*Primary Examiner*—A. Lionel Clingman
*Attorney, Agent, or Firm*—Bert J. Lewen

[57] ABSTRACT

A method for treating natural textile fibres and synthetic polyamide fibres to enhance their affinity for disperse dyestuffs which comprises treating the fibres with an aqueous solution or dispersion of an arylating agent. The arylating agent contains both a benzene or naphthalene ring and a reactive group, such as a halotriazine group. The fibres may be treated by exhaustion from long liquors or by padding, and the affinity for disperse dyestuffs is considerably increased thereby.

12 Claims, No Drawings

TREATMENT OF FIBERS WITH ARYLATING AGENTS TO ENHANCE DISPERSE DYEABILITY

This invention relates to a method of treating textiles, and in particular relates to a method for treating cellulosic, keratinous and polyamide textiles to increase their affinity for disperse dyes.

Keratinous fibres such as wool, and natural cellulosic fibres such as cotton do not normally exhibit any marked affinity for disperse dyestuffs. Again attempts to dye these fibres with disperse dyes result in poor colour yields, dull shades and poor wet and light fastness. Disperse dyestuffs are used largely with synthetic fibres such as polyesters and are therefore commonly available. Furthermore, disperse dyes are often sublimable and form the basis of the well known 'transfer printing' process in which papers are printed with a design using disperse dye and these papers may then be subsequently used to colour the textile fabric merely by placing the paper and the fabric together and heating in a press for a short period of time, typically half a minute.

Synthetic polyamide fibres ('nylon') have apparently adequate affinity for disperse dyes but the wash fastness of dyeings and prints of these dyes on this substrate is inadequate.

The invention seeks to provide a method of increasing the affinity of these fibres to disperse dyestuffs and to allow strong wet-fast dyeings and prints to be produced. In accordance with the broadest aspect of the present invention there is provided a method of treating natural textile fibres and synthetic polyamide fibres to enhance their affinity for disperse dyestuffs which comprises treating the fibres with an aqueous solution or dispersion of an arylating agent. The arylating agent may contain one or more benzene or naphthalene residues and is covalently bonded to the fibre by a suitable reactive group.

The amount of arylating agent employed is preferably between 2 and 20% on weight of fibre (OWF) and is conveniently in the range 6 to 12% OWF.

The arylating agent may be applied either by exhaustion from long liquors or by padding. In the former case the arylating agent is dissolved or dispersed in water, preferably in the presence of a non-ionic surfactant and a buffer. The textile fabric may be immersed in the bath which is raised to the boil and boiling continued for a period of, for example, from 10 minutes to 2 hours. Where the arylating agent is applied by padding, the agent is dispersed or dissolved in water together with a swelling agent for the textiles, for example, urea and a thickener. The fabric may be padded, steamed to fix the reagent and rinsed to remove unfixed arylating agent or alternatively padded with the reactive agent, batched for periods up to 48 hours to allow reaction to occur and then rinsed to remove unfixed reagent.

The arylating agent may be any suitable compound which contains both one or more benzene rings and a reactive group, such as substituted halo triazine ring, vinyl sulphone ring, carbamoyl sulphonate, thio-ester, dithioesters groups, α-bromoacrylamido, or 2,4-difluoro-5-chloro pyrimidine groups.

The invention further provides novel arylating agents having the following structural formulae

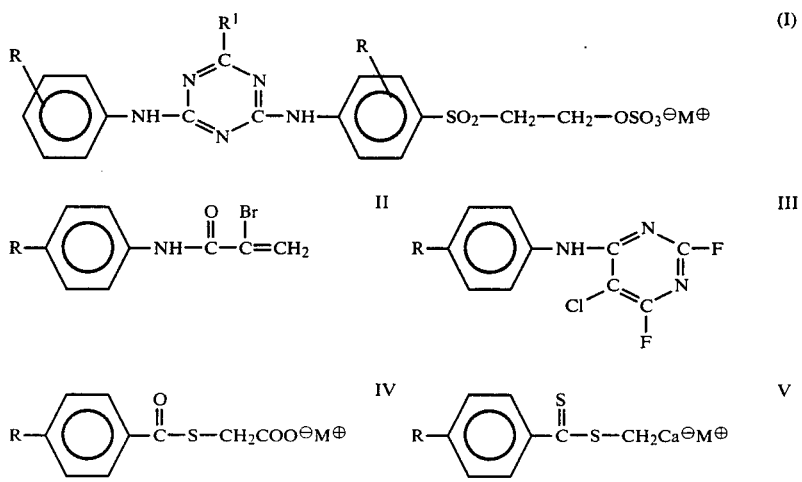

wherin R is hydrogen, alkyl, alkoxy, 4-sulphatoethyl sulphone or halogen, M is a metal cation, and R¹ is halogen or aminobenzene-4-sulphato ethyl sulphone.

Preferably R is a short chain alkyl group of less than four carbon atoms. Where R is a long chain alkyl group, e.g. of about twelve carbon atoms, affinity for disperse dyes is good but the wash-fastness of the dyed fabric is less than with short chain substituents. R¹ is preferably chlorine.

Specific arylating agents useful in the practice of the invention are given below.

AI

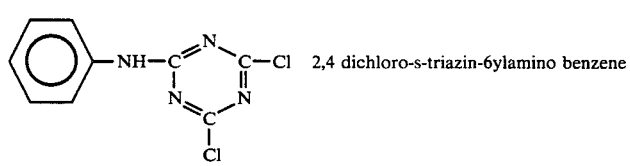

2,4 dichloro-s-triazin-6ylamino benzene

-continued

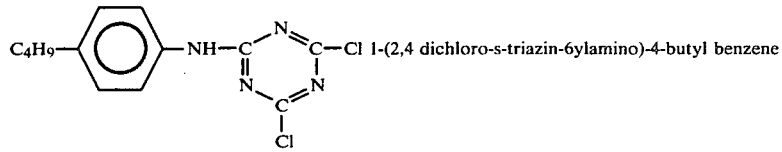 1-(2,4 dichloro-s-triazin-6ylamino)-4-butyl benzene  AII

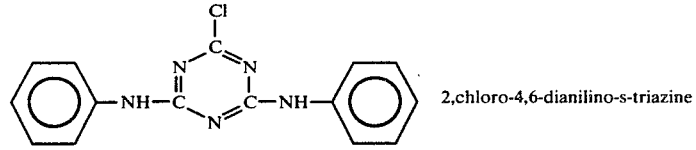 2,chloro-4,6-dianilino-s-triazine  AIII

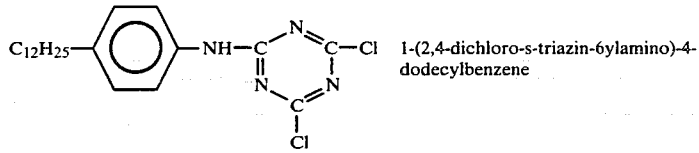 1-(2,4-dichloro-s-triazin-6ylamino)-4-dodecylbenzene  AIV

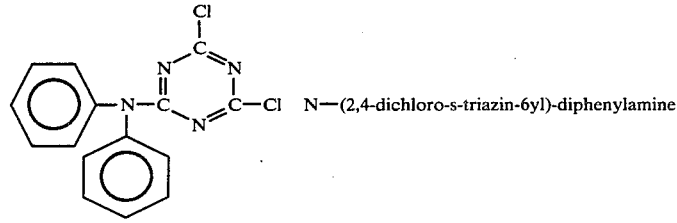 N—(2,4-dichloro-s-triazin-6yl)-diphenylamine  AV

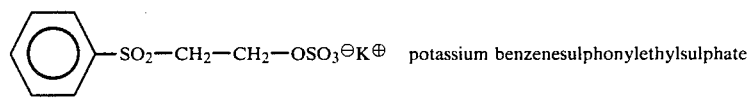 potassium benzenesulphonylethylsulphate  BI

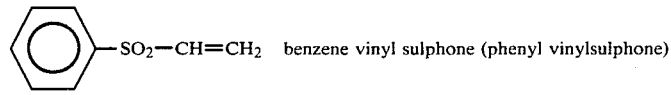 benzene vinyl sulphone (phenyl vinylsulphone)  BII

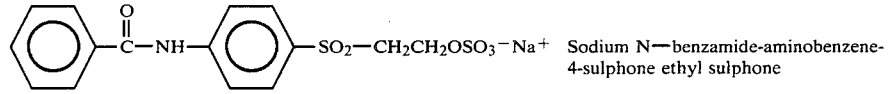 Sodium N—benzamide-aminobenzene-4-sulphone ethyl sulphone  BIII

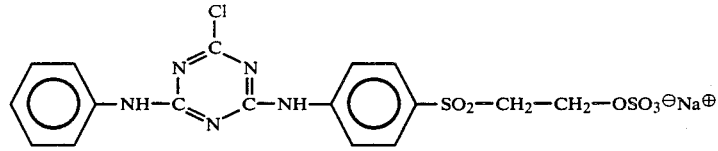
sodium 1'-(2-chloro-4-anilino-s-triazin-6yl)-amino benzene 4'-sulphatoethylsulphone  AB

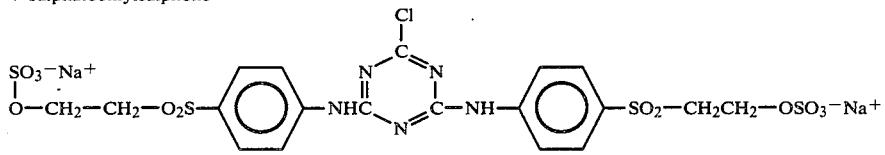  BAB

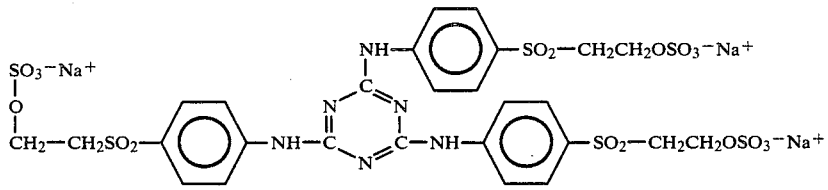

-continued

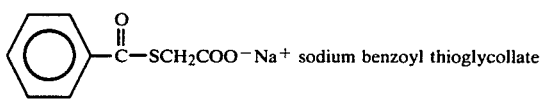 sodium benzoyl thioglycollate  CI

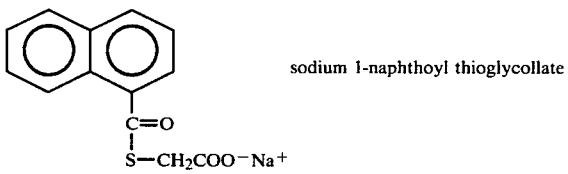 sodium 1-naphthoyl thioglycollate  CII

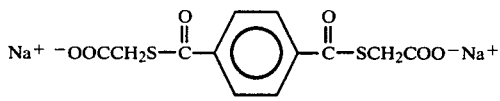 disodio terephthaloyl-bisthioglycollate  CIII

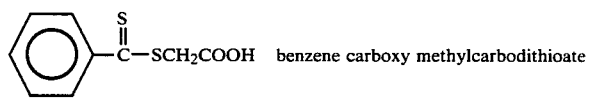 benzene carboxy methylcarbodithioate  D

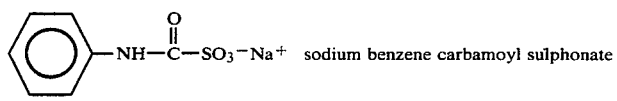 sodium benzene carbamoyl sulphonate  E

The compounds may be applied either from aqueous solutions or from aqueous dispersions. The latter may be prepared by milling the insoluble compound with an anionic dispersing agent, e.g. Matexil DA-AC (ICI), which is believed to be the disodium salt of methylene dinaphthalene sulphonic acid.

These dispersions may be applied to wool, nylon or cotton fabrics by padding or long liquor exhaustion techniques. Application levels of at least 10% are envisaged for wool and cotton but for the diphenyl derivatives lower amounts will suffice. Following application the fabrics are rinsed clear of unreacted compound by washing at 50° C. in the presence of a nonylphenol ethylene oxide condensate such as Lissapol N (ICI).

According to the present invention there is also provided a method of producing a compound of formula I which comprises reacting a compound of formula (V) with an alkali metal salt of a compound of formula V and separating the reaction product.

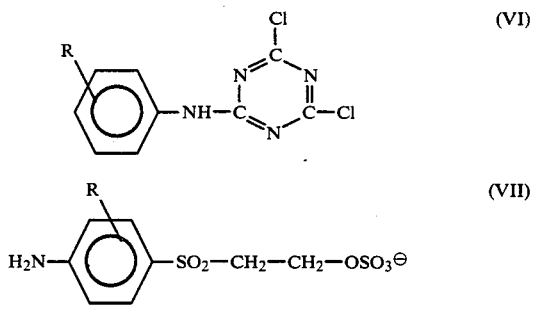

wherin R has the meaning given above.

It has also been found that the method of treating wool fabrics with reactive arylating agents of the invention imparts a high level of resistance to felting at treatment levels up to 20% OWF. Useful results are achieved in the 10–15% OWF region. Furthermore the heat settability of wool fibres is improved using similar treatment levels; and improved wet and dry wrinkle recovery is imparted to cellulosic fabrics using a degree of arylation between 5–20% OWF.

The following examples illustrate the process of this invention.

EXAMPLE 1

The reactive hydroprobe A1 (2,4-dichlor-s-triazin-6-yl amino benzene) was prepared in the following manner:

0.1M of cyanuric chloride was dissolved in acetone (80 ml) and chilled to 0°–5° C. in an ice/salt bath. To this solution was added dropwise with good stirring 0.1M aniline along with a calculated amount of sodium carbonate dissolved in 100 ml of water to neutralise the HCl produced in the reaction. After 1 hour the reaction was judged to be complete (no further change in pH) and the acetone layer separated from the residues. On evaporation of the acetone layer, compound A1 was recovered as a white crystalline solid.

The compound was dispersed in the following manner:

30 g A1
30 g Matexil DA-AC (anionic dispersant)
10 g Symperonic PE 39/40 (non-ionic dispersant)
50 g Water and milled on the laboratory Eiger mill for 1 hour to give a 25% w/w aqueous dispersion. This dispersion was applied to wool by two different techniques.

(a) Exhaustion Application

The above dispersion was applied to wool fabric at 20% o.w.f. active compound in the presence of 20% o.w.f. Lissapol N (nonyl phenol nona-oxyethylene glycol) and sodium dihydrogen phosphate/disodium hydrogen phosphate buffers, set to give a bath pH of 6.8. The liquor to goods ratio was adjusted to 20:1. The bath was raised to the boil over 30 minutes and boiling continued a further 30 minutes. Unreacted or hydrolysed compound was removed by 'soaping off' at the boil for 10 minutes with 6 g/l Lissapol N. Wool treated in this way was found to increase in weight by 10%.

The above pretreated wool was sublimation transfer printed for 30 seconds at 200° C. in a Kannegiesser press with a disperse dye transfer printing paper normally employed for printing polyester fabrics (dyes used were Cl Disperse Red 60 and Disperse Yellow 3). For comparison a piece of untreated wool as control was also transfer printed with the same paper. The prints obtained on the wool pretreated with Al were observed to be very much stronger than the prints on untreated wool—on steaming the prints for 30 minutes at 100° C. a further intensification of colour resulted; these prints were tested for wash fastness using the ISO2 test and for light fastness. On the pretreated wool a change in shade of 4–5 was recorded in the ISO2 test whereas the corresponding change in shade on the printed untreated wool was 1—indicating very low wet fastness in this case. Light fastness on the printed pretreated wool was assessed as 5 and on the printed untreated wool as 3.

(b) Pad Application

The above dispersion was applied to wool fabric from the following pad liquor:
500 g/kg dispersion
200 k/kg Urea
8 g/kg Solvitose OFA (Thickener)

Following padding to 100% wet pick up samples were dried and steamed for 30 minutes at 100° C. Thorough rinsing was carried out to remove unfixed hydroprobe. The weight gain of the treated fabric was determined as 11%.

Fabric treated in the above manner was transfer printed with the same disperse dye papers described above. Again good colour yields with good wet and light fastness properties were obtained.

Fabric samples prepared by both methods (a) and (b) were dyed with the disperse dye Terasil Yellow X-5R (Ciga-Geigy) at a level of 3% OWF. Dyeing was carried out at a liquor ratio of 20:1 in the presence of 2 g/l Lissapol N, raising to the boil and boiling for 30 minutes. For comparison untreated wool was included in the dyebath. At the end of dyeing the bath was practically clear of dye indicating good affinity for the fibre. The dyed samples were thoroughly rinsed, dried and visually assessed; it was clear that the pretreated wool fabrics had absorbed the disperse dye to give a full yellow, level, well-penetrated dyeing—the untreated wool was only lightly dyed.

Surprisingly the wool samples treated by methods (a) and (b) with compound Al also showed high affinity for cationic dyes. These dyes were applied by transfer printing (200° C., 30") from papers printed with their sublimable carbinol base derivatives—following steaming, prints of good wet and light fastness were obtained, in contast to the poor prints and low fastness properties obtained on an untreated wool sample.

Wools treated by methods (a) and (b) were also observed to be resistant to felting. The degree of shrink resistance was determined by testing in phosphate pH7 buffer for 3 hours at 50° C. in an International Cubex machine at a liquor to goods ratio of 15:1. The following results were obtained:

| Treatment | % Area Felting Shrinkage |
|---|---|
| NONE | 60 |
| (a) | 5 |
| (b) | 5 |

EXAMPLE 2

The methods of example 1 were followed but in this case reactive hydrophobe AII was employed. Very similar results were obtained but it was noted that at lower add-ons of compounds AII higher yields of disperse dyes could be obtained than with compound Al.

EXAMPLE 3

The methods of Example 1 were followed using reactive hydrophobe AIII. Again, similar results were obtained.

EXAMPLE 4

This example demonstrates the possibility of applying these reactive hydrophobes in the same bath as a disperse dye improving the dye yield and fastness on wool.

A dyebath was set with 2% owf Terrasil yellow X-5R and 20% owf reactive hydrophobe Al. To the bath was added a swatch of wool fabric and the bath raised to boiling over 30 minutes and boiling continued for a further 1 hour. Complete exhaustion of the bath was noted and the dyeing was observed to be level and fast to wet treatments.

By way of contrast the above procedure was repeated but omitting the reactive hydrophobe Al; in this case the bath exhaustion was very poor, the final dyeing being weak in shade and showing poor fastness to subsequent wet treatments.

EXAMPLE 5

It is difficult to dye synthetic polyamide fibres completely level to a high standard of wet fastness due to the problem known as barre. It is well known that disperse dyes have affinity for these fibres and overcome the barre problem but unfortunately show poor wet fastness when dyed with this class of dye. However, if a dispersion of the reactive hydrophobes are added to the dyebath in accordance with the invention, towards the end of dyeing, then the fastness to wet treatments is increased to a satisfactory level.

Nylon 6 knitted fabric was dyed to a green shade using 0.4% owf Cl Disperse Yellow 3 and 0.3% owf Cl Disperse Blue 14. After dyeing at the boil for 60 minutes it was observed that the green dyeing was completely level and free of the fault known as barre; half of the sample was returned to the boiling dyebath and aftertreated with 6% owf compound Al for a further 30 minutes at the boil. Samples of the aftertreated and non aftertreated dyed fabrics were tested according to the ISO2 test for wash fastness—the aftertreated sample rated 4 on change of shade which is good, whereas the original sample rated only 2–3.

EXAMPLE 6

Compound AB was applied to cotton fabric by padding with the following pad liquor:
150 g/l AB
100 g/l urea 10 g/l Lissapol N.
The fabric was batched for 3 hours at room temperature, dried and repadded with an alkaline pad liquor:
181 g/l Crossfields No. 1 silicate
117 g/l sodium hydroxide (10% wv) solution
Fixation under these alkaline conditions was achieved by batching for 24 hours; the fabric was then washed off and dried. When transfer printed with the disperse dye papers employed in Example 1 bright fast prints were achieved. By way of comparison a similar transfer print on unmodified cotton gave very low colour yields with poor wet fastness.

EXAMPLE 7

A pad liquor was prepared containing the following:
Sodium 1-naphthoyl thioglycollate (CII) 100 g/l
Sodium carbonate 30 g/l
Lissapol N 10 g/l
Wool serge fabric was padded through this liquor rolled up and batched in a polythene wrapper for 24 hours at 20° C. After this time the fabric was well rinsed with water and dried.
The treated fabric was then transfer printed (200° C. for 30 seconds) with disperse dyes as described in Example 1. Following steaming of the print for 30 minutes at 100° C. a brilliant print of good wet fastness was obtained.

EXAMPLE 8

Compound BAB was incorporated into the following pad liquor:
BAB 150 g/l
Urea 100 g/l
Lissapol N 10 g/l
Cotton fabric was padded through this liquor on a mangle set to give 70% wet pick up and this impregnated fabric was batched for 2 hours to allow reagent diffusion. Following batching the sample was dried and repadded with the following pad liquor:
181 g/l Crosfields No. 1 silicate
117 g/l Sodium Hydroxide solution (10% to 70% wet pick up.
The fabric was batched, covered in polythene film and stored at room temperature for 24 hours. After this time the fabric was thoroughly washed off in hot water (70° C.) and then repeatedly in cold running water.
After drying the fabric was transfer printed at 200° C. for 30 seconds with a paper preprinted with disperse dyes. The colour yield, clarity and wet fastness prpoerties of this pring were assessed as excellent.

I claim:
1. The method of treating cellulosic and wool fibres to enhance their affinity to disperse dyestuffs which comprises treating the fibres with an aqueous solution or a dispersion of an arylating agent selected from the group: 2,4 dichloro-s-triazin-6ylaminobenzene; 1-(2,4 dichloro-s-triazin-6ylamino)-4-butyl benzene; 2,chloro-4,6-dianilino-s-triazine; 1-(2,4-dichloro-s-triazin-6ylamino)-4-dodecyl benzene; N-(2,4-dichloro-s-triazin-6yl)diphenylamine; potassium benzenesulphonylethyl sulphate; benzene vinyl sulphone; sodium N-benzamidoaminobenzene-4-sulphato ethyl sulphone; sodium 1'-(2-chloro-4-anilino-s-triazin-6yl)-amino benzene 4'-sulphato ethyl sulphone; sodium 2-chloro-4,6-di(amino benzene 4'-sulphato ethyl sulphone)-s-triazine; sodium 2,4,6-tri(amino benzene 4'-sulphato ethyl sulphone)-s-triazine; sodium benzoyl thioglycollate; sodium 1-naphthoyl thioglycollate; disodio terephthaloyl-bis thioglycollate; benzene carboxymethylcarbodithioate; and sodium benzene carbamoyl sulphonate.

2. The method of treating cellulosic and wool fibres to enhance their affinity to disperse dyestuffs which comprises treating the fibres with an aqueous solution or a dispersion of an arylating agent selected from the group:

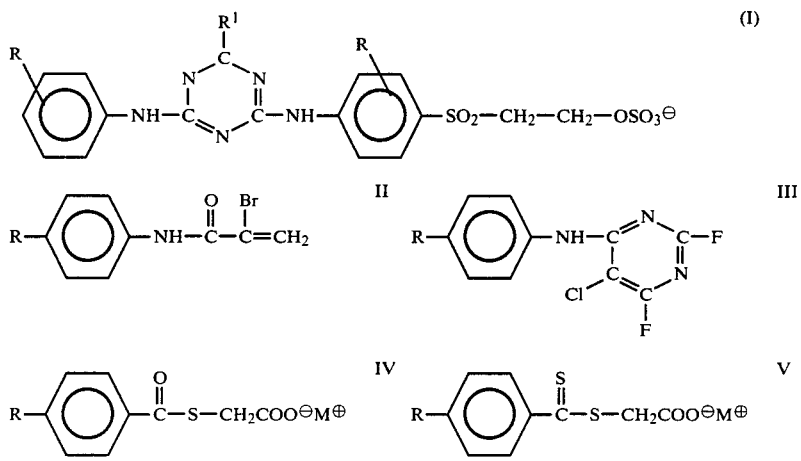

wherein R is hydrogen, alkyl, alkoxy, 4-sulphatoethyl sulphone or halogen, M is a metal cation, and $R^1$ is halogen or aminobenzene-4-sulphato ethyl sulphone.

3. A method of claim 1 or 2 in which the amounts of arylating agent employed is between 2 and 20% on weight of fibre.

4. A method as claimed in claim 3 in which the amount of arylating agent employed is between 6 and 12% on weight of fibre.

5. A method of claim 4 in which the arylating agent is applied by exhaustion from long liquor.

6. A method of claim 4 in which the arylating agent is applied by padding.

7. A method as claimed in claim 5 in which the arylating agent is dissolved or dispersed in water in the presence of a non-ionic surfactant and a buffer after which the textile fabric is immersed in the solution or dispersion which is raised to the boil and boiling continued for a period of from ten minutes to two hours.

8. A method as claimed in claim 6 in which the arylating agent is dispersed or dissolved in water together with a swelling agent for the textile and a thickener and, after the fabric has been padded, it is steamed and rinsed to remove unfixed arylating agent.

9. A method as claimed in claim 8 in which, after padding, the fabric is batched for from 2 to 24 hours at room temperature to allow diffusion and reaction to occur.

10. A method as claimed in claim 8 in which, after padding, the fabric is treated for between 0.5 and 5 minutes at a temperature in the range 150° to 250° C.

11. A method as claimed in claim 10 in which the time is about 1 minute.

12. A method as claimed in claim 6 or 11 in which the temperature is in the range of 180° to 200° C.

* * * * *